(12) United States Patent
Guertin et al.

(10) Patent No.: US 6,642,381 B2
(45) Date of Patent: Nov. 4, 2003

(54) PYRIMIDO[5,4-E][1,2,4]TRIAZINE-5,7-DIAMINE COMPOUNDS AS PROTEIN TYROSINE PHOSPHATASE INHIBITORS

(75) Inventors: Kevin Richard Guertin, Verona, NJ (US); Lina Quattrocchio Setti, San Mateo, CA (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/315,769

(22) Filed: Dec. 10, 2002

(65) Prior Publication Data

US 2003/0153756 A1 Aug. 14, 2003

Related U.S. Application Data

(60) Provisional application No. 60/399,110, filed on Jul. 26, 2002, and provisional application No. 60/343,937, filed on Dec. 27, 2001.

(51) Int. Cl.$^7$ ............................................. C07D 487/04
(52) U.S. Cl. ........................................ 544/184; 544/112
(58) Field of Search ................................. 544/184, 112

(56) References Cited

FOREIGN PATENT DOCUMENTS

| WO | WO 99 65909 | 12/1999 |
|----|----|----|
| WO | WO 0220525 | 3/2002 |

OTHER PUBLICATIONS

Moeller, et al. Protein Tyrosine Phosphatases (PTPs) as Drug Targets: Inhibitors of PTP–1B for the Treatment of Diabetes, Drug Discovery & Development (2000), vol. 3(5) pp. 527–540.

Zhang, Zhong–Yin, Protein Tyrosine Phosphatases: Prospects for Therapeutics, Current Opinion in Chemical Biology (2001), vol. 5: pp. 416–423.

Ansel, et al. Pharmaceutical Dosage Forms & Drug Delivery Systems (6$^{th}$ Ed. 1995) p. 196.

Coleman, Diabetologia 14, pp. 141–148 (1978).

Barford, et al. J. Mol. Biol. (1994) 239, pp. 726–730.

Harder, et al. (1994) Biochem. J., vol. 298, pp. 395–401.

Surwit, et al. Diabetes (1988) vol. 37: 1163–67.

Henrik Sune Andersen, et al., Journal of Biological Chemistry, vol. 275, No. 10, pp. 7101–7108 (2000).

*Primary Examiner*—John M. Ford
(74) *Attorney, Agent, or Firm*—George W. Johnston; Dennis P. Tramaloni; Eileen M. Ebel

(57) ABSTRACT

The invention relates to pyrimido[5,4-e][1,2,4]triazine-5,7-diamine compounds which are useful for inhibiting protein tyrosine phosphatases, particularly PTP1B.

17 Claims, No Drawings

PYRIMIDO[5,4-E][1,2,4]TRIAZINE-5,7-DIAMINE COMPOUNDS AS PROTEIN TYROSINE PHOSPHATASE INHIBITORS

CROSS-REFERENCE TO RELATED APPLICATIONS

This application claims the benefit of U.S. Provisional Patent Application Serial No. 60/399,110, filed Jul. 26, 2002, and No. 60/343,937, filed Dec. 27, 2001.

FIELD OF THE INVENTION

The invention relates to pyrimido[5,4-e][1,2,4]triazine-5,7-diamine compounds which are useful for inhibiting protein tyrosine phosphatases, particularly PTP1B.

BACKGROUND OF THE INVENTION

Protein tyrosine phosphatases (PTPases) are key enzymes in the processes that regulate cell growth and differentiation. The inhibition of these enzymes can play a role in the modulation of multiple signaling pathways in which tyrosine phosphorylation dephosphorylation plays a role. PTP1B is a particular protein tyrosine phosphatase that is often used as a prototypical member of that class of enzymes.

PTPase inhibitors are recognized as potential therapeutic agents for the treatment of diabetes. See, e.g. Moeller et al., 3(5):527–40, Current Opinion in Drug Discovery and Development, 2000; or Zhang, Zhong-Yin, 5:416–23, Current Opinion in Chemical Biology, 2001.

SUMMARY OF THE INVENTION

It has been discovered that compounds of the formula:

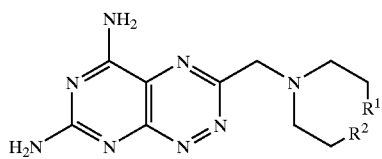

I and the pharmaceutically acceptable salts thereof, wherein $R^1$ and $R^2$ are as defined below, inhibit protein tyrosine phosphatases, particularly PTP1B and so would be useful for lowering blood glucose concentrations in mammals.

DETAILED DESCRIPTION OF THE INVENTION

DEFINITIONS

As used in the specification, the term "lower alkyl", alone or in combination, means a straight-chain or branched-chain alkyl group containing a maximum of six carbon atoms, such as methyl, ethyl, n-propyl, isopropyl, n-butyl, sec-butyl, isobutyl, tert-butyl, n-pentyl, n-hexyl and the like. Lower alkyl groups may be unsubstituted or substituted by one or more groups selected independently from cycloalkyl, nitro, aryloxy, aryl, hydroxy, halogen, cyano, lower alkoxy, lower alkanoyl, lower alkylthio, lower alkyl sulfinyl, lower alkyl sulfonyl and substituted amino. Examples of substituted lower alkyl groups include 2-hydroxyethyl, 3-oxobutyl, cyanomethyl and 2-nitropropyl.

The term "cycloalkyl" means an unsubstituted or substituted 3- to 7-membered carbocyclic ring. Substituents useful in accordance with the present invention are hydroxy, halogen, cyano, lower alkoxy, lower alkanoyl, lower alkyl, aroyl, lower alkylthio, lower alkyl sulfinyl, lower alkyl sulfonyl, aryl, heteroaryl and substituted amino.

The term "lower alkoxy" means a straight-chain or branched-chain alkoxy group containing a maximum of six carbon atoms, such as methoxy, ethoxy, n-propoxy, isopropoxy, n-butoxy, tert-butoxy and the like.

The term "lower alkylthio" means a lower alkyl group bonded through a divalent sulfur atom, for example, a methyl mercapto or a isopropyl mercapto group.

The term "aryl" means a mono- or bicyclic aromatic group, such as phenyl or naphthyl, which is unsubstituted or substituted by conventional substitutent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanyoyl, aroyl, aryl alkynyl, lower alkynyl and lower alkanoylamino. The especially preferred substituents are lower alkyl, lower alkoxy, hydroxy, halogen, cyano and perfluoro lower alkyl. Examples of aryl groups that may be used in accordance with this invention are phenyl, p-tolyl, p-methoxyphenyl, p-chlorophenyl, m-hydroxy phenyl, m-methylthiophenyl, 2-methyl-5-nitrophenyl, 2,6-dichlorophenyl, 1-naphthyl and the like.

The term "lower alkyl-aryl" means a lower alkyl group as hereinbefore defined in which one or more hydrogen atoms is/are replaced by an aryl group as hereinbefore defined. Any conventional lower alkyl-aryl may be used in accordance with this invention, such as benzyl and the like.

The term "lower alkoxy-aryl" means a lower alkoxy group as hereinbefore defined in which one or more hydrogen atoms is/are replaced by an aryl group as hereinberfore defined. Any conventional lower alkoxy-aryl may be used in accordance with this invention, such as benzyloxy.

The term "lower alkoxycarbonyl" means a lower alkoxy group bonded via a carbonyl group. Examples of alkoxycarbonyl groups are ethoxycarbonyl and the like.

The term "pharmaceutically acceptable salts" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp: 196 and 1456–1457.

The present invention comprises compounds of the formula I:

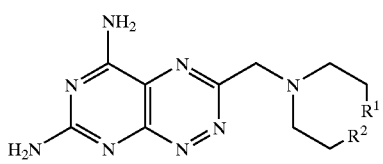

and the pharmaceutically acceptable salts thereof. In accordance with the invention, $R^1$ and $R^2$ are individually selected from the group consisting of hydrogen, or $R^1$ and $R^2$ together form a bond, —$CH_2$—, —O—, —NH— or —N—$R^3$, $R^3$ is lower alkyl or —$CH_2$—Ar, and Ar is selected from the group consisting of unsubstituted phenyl; unsubstituted naphthyl; phenyl mono- or bi-substituted with lower alkyl, lower alkoxy, aryl, cycloalkyl, lower alkyl-aryl, lower alkoxy-aryl, lower alkyl-cycloalkyl, lower alkoxy-cycloalkyl, halo, cyano or trifluoromethyl; and naphthyl mono- or bi-substituted with lower alkyl, lower alkoxy, aryl, cycloalkyl, lower alkyl-aryl, lower alkoxy-aryl, lower alkyl-cycloalkyl, lower alkoxy-cylcoalkyl or halo.

Among the compounds of formula 1, preferred compounds are those of formula II:

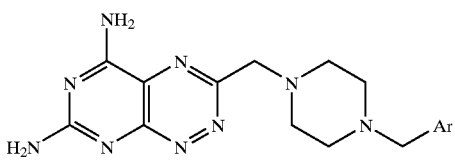

where Ar is selected from the group consisting of unsubstituted phenyl; unsubstituted naphthyl; phenyl mono- or bi-substituted with lower alkyl, lower alkoxy, aryl, cycloalkyl, lower alkyl-aryl, lower alkoxy-aryl, lower alkyl-cycloalkyl, lower alkoxy-cycloalkyl, halo, cyano or trifluoromethyl; and naphthyl mono- or bi-substituted with lower alkyl, lower alkoxy, aryl, cycloalkyl, lower alkyl-aryl, lower alkoxy-aryl, lower alkyl-cycloalkyl, lower alkoxy-cylcoalkyl or halo.

In one preferred embodiment of the compounds of formula II, Ar is unsubstituted phenyl or unsubstituted naphthyl.

In another preferred embodiment of the compounds of formula II, Ar is phenyl mono-substituted with lower alkyl, lower alkoxy, aryl, cycloalkyl, lower alkyl-aryl, lower alkoxy-aryl, halo, cyano or trifluoromethyl.

In yet another preferred embodiment of the compounds.of formula II, Ar is phenyl mono-substituted with lower alkyl, lower alkoxy, halo, cyano or trifluoromethyl.

In still another preferred embodiment of the compounds of formula II, Ar is phenyl bi-substituted with lower alkyl, lower alkoxy, halo or cyano.

In a further preferred embodiment of the compounds of formula II, Ar is naphthyl mono-substituted with lower alkyl, lower alkoxy, lower alkyl-aryl, lower alkoxy-aryl or halo.

In yet a further preferred embodiment of the compounds of formula II, Ar is naphthyl mono-substituted with lower alkyl, lower alkoxy or halo.

In still a further preferred embodiment of the compounds of formula II, Ar is naphthyl bi-substituted with lower alkyl, lower alkoxy or halo.

The compounds of the invention can exist as stereoisomers and diastereomers, all of which are encompassed within the scope of the present invention.

The compounds of the invention inhibit PTP1B in vitro and have been shown to lower blood glucose levels in vivo. Thus, the compounds of the present invention would be useful for the treatment of diabetes.

The compounds of the invention can be administered orally, rectally, or parentally, e.g. intravenously, intramuscularly, subcutaneously, intrathecally or transdermally; or sublingually, or as opthalmalogical preparations. Capsules, tablets, suspensions or solutions for oral administration, suppositories, injection solutions, eye drops, salves or spray solutions are examples of administration forms.

Intravenous, intramuscular, oral or inhalation administration are preferred forms of use. The dosages in which the compounds of the invention are administered in effective amount depends on the nature of the specific active ingredient, the age and requirements of the patient and the mode of administration. Dosages may be determined by any conventional means, e.g., by dose-limiting clinical trials. In general, dosages of about 0.1 to 100 mg/kg body weight per day are preferred, with dosages of 1–25 mg/kg per day being particularly preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of the invention. The compounds of the invention may be prepared by any conventional means. A particular method is described in the following Schemes 1 through 3.

SCHEME 1

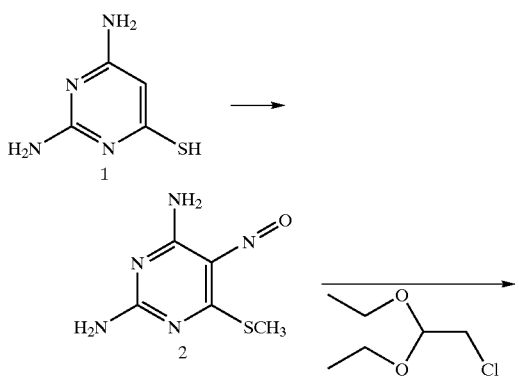

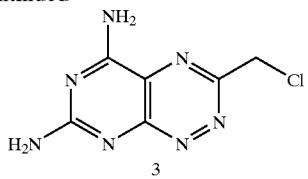

The intermediate chloromethyl compound 3 is prepared from commercially available 2,4-diamino-2-mercaptopyrimidine hemisulfate 1 as outlined in Scheme 1. S-methylation of 1 (e.g., using sodium hydroxide and methyliodide) followed by nitrosylation under standard conditions (e.g., using sodium nitrate with acetic acid at about 50° C.) provides the intermediate arylnitrosyl derivative 2. Displacement of the thiomethyl group of 2 with hydrazine in a suitable solvent such as dimethylformamide at room temperature followed by condensation with commercially available chloromethylacetaldehyde diethyl acetal under acidic conditions (e.g., HCl) with heating (e.g., about 85° C.) affords the chloromethyl derivative 3.

SCHEME 2

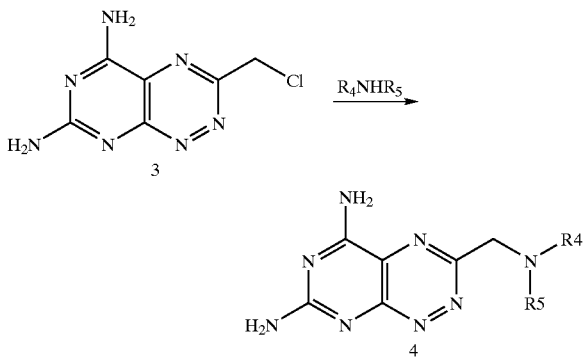

The chloromethyl derivative 3 may then be reacted with a variety of known amines in a suitable solvent such as ethanol with heating (e.g., at about 80–100° C.) to provide the corresponding aminomethyl derivatives 4 as outlined in Scheme 2. For amines $R^4NR^5$ of Scheme 2, $R^4$ is —$CH_2CH_2R_1$ and $R^5$ is —$CH_2CH_2R_2$, and $R^1$ and $R^2$ are as previously defined.

SCHEME 3

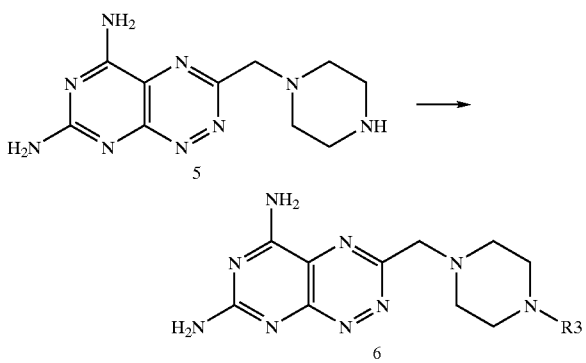

The piperazine derivative 5 (e.g., derivative 4 where $R^4$ and $R^5$ together form a —$CH_2CH_2NHCH_2CH_2$— moiety) is prepared from chloromethyl derivative 3 and piperazine as outlined in Scheme 2. Alkylation of derivative 5 with a variety of known alkyl halides (e.g., $R^3Br$ or $R^3I$, where $R^3$ is defined above) is carried out in a suitable solvent such as dimethylformamide using a suitable base such as potassium carbonate at room temperature to provide the dialkylated piperazine derivatives 6 as outlined in Scheme 3.

EXAMPLES

Example 1

6-Methylthio-5-nitroso-pyrimidine-2,4-diamine

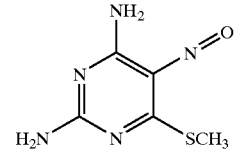

Step 1: To a stirred solution of 105 g KOH in 1 L of water was added 2,4-diamino-6-mercaptopyrimidine hemisulfate 1 (70.0 g) followed by methyl iodide (91 mL). The resulting mixture was vigorously stirred for 4 h and then the solid precipitate was filtered off, washed with water and air dried overnight to give 54.0 g of 6-Methylthio-pyrimidine-2,4-diamine as a tan colored solid.

$^1$H NMR (DMSO-$d_6$, ppm): 6.20 (s, 2H), 5.90 (s, 2H), 5.55 (s, 1H), 2.30 (s, 3H).

Step 2: To a stirred suspension of 6-Methylthio-pyrimidine-2,4-diamine (50.0 g; 321 mmol) in water (1000 mL) was added 500 mL of 2N acetic acid. The mixture was warmed to 50° C. and $NaNO_2$ solution was added (24.0 g; 353 mmol in 200 mL $H_2O$) rapidly. After 1 hr at 50° C., the deep Blue/purple mixture was allowed to cool to room temperature and filtered. The blue/purple solid was washed several times with water and finally washed with ether. The solid was allowed to air dry to give 51.0 g of 6-Methylthio-5-nitroso-pyrimidine-2,4-diamine 2 as blue/purple solid.

$^1$H NMR (DMSO-$d_6$, ppm): 9.70 (s, 1H), 8.10 (s, 1H), 7.95 (m, 2H), 2.43 (s, 3H).

Example 2

6-Hydrazino-5-nitroso-pyrimidine-2,4-diamine

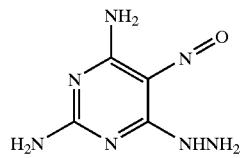

Hydrazine hydrate (55% solution, 14.5 mL) was added rapidly to a suspension of (12.0 g; 64.9 mmol) of 6-Methylthio-5-nitroso-pyrimidine-2,4-diamine 2 in DMF at room temperature. The mixture was allowed to stir overnight and then the bright pink mixture was filtered and the solid washed several times with DMF followed by ether and then air dried to give 9.53 g of 6-Hydrazino-5-nitroso-pyrimidine-2,4-diamine as bright pink solid.

$^1$H NMR (DMSO-$d_6$, ppm): 8.00 (s, 1H), 7.40 (s, 1H), 7.05 (m, 2H), 5.35 (m, 2H).

Example 3

3-Chloromethyl-pyrimido[5,4-e][1,2,4]triazine-5,7-diamine

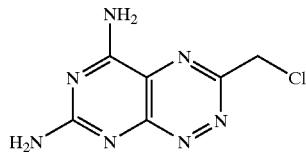

Concentrated HCl (14 mL) was added to stirred ice cooled DMF (350 mL) followed by 7.14 g of 6-Hydrazino-5-nitroso-pyrimidine-2,4-diamine. After 5 min., chloroacetaldehyde diethylacetal (15.4 mL) was added over a ca. 2 min. period. The cooling bath was removed and the mixture allowed to come to room temperature. After 1 h, the mixture was warmed to 85° C. for 1.5 h and then allowed to cool to room temp over a 2.5 h period. The mixture was filtered to remove a small amount of brown insoluble material, the filtrate made alkaline with concentrated $NH_4OH$ solution and then diluted with an equal volume of water. The mixture was set aside for 1 h and then filtered to collect the orange/brown solid which was further dried in vacuo over $P_2O_5$ to give 3.50 g of 3-Chloromethyl-pyrimido[5,4-e][1,2,4]triazine-5,7-diamine 3.

$^1$H NMR (DMSO-$d_6$, ppm): 8.25 (s, 2H), 7.95 (s, 1H), 7.30 (bs, 1H), 5.02 (s, 2H).

Example 4

3-Piperazin-1-ylmethyl-pyrimido[5,4-e][1,2,4]triazine-5,7-diamine

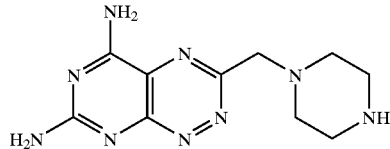

A mixture of 3-Chloromethyl-pyrimido[5,4-e][1,2,4]triazine-5,7-diamine 3 (2.00 g; 9.5 mmol) and piperazine (2.50 g; 29 mmol) in absolute ethanol was heated to 100° C. in a sealed tube for 4 h. The mixture was then allowed to cool to room temperature and evaporated. The crude product was purified by reverse phase HPLC (Rainin $C_{18}$, 0% $CH_3CN$ to 30% $CH_3CN$ gradient, $CH_3CN/H_2O$, 0.1% TFA) and the bright yellow fractions containing the product were lyophilized after removal of $CH_3CN$ in vacuo to give 1.44 g of yellow colored 3-Piperazin-1-ylmethyl-pyrimido[5,4-e][1,2,4]triazine-5,7-diamine 5 as the trifluoroacetate salt.

$^1$H NMR (DMSO-$d_6$, ppm): 9.55 (s, 1H), 9.40 (s, 1H), 8.80 (s, 2H), 8.45 (s, 1H), 4.15 (s, 2H), 3.10 (m, 4H), 2.80 (m, 4H).

Example 5

3-Diethylaminomethyl-pyrimido[5,4-e][1,2,4]triazine-5,7-diamine

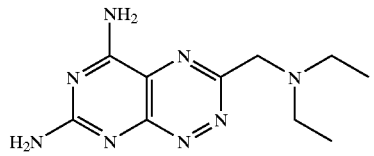

A mixture of 3-Chloromethyl-pyrimido[5,4-e][1,2,4]triazine-5,7-diamine 3 (200 mg; 0.95 mmol) and diethylamine (2.00 mL) in absolute ethanol (2.0 mL) was heated to 100° C. in a sealed tube for 5 h. The mixture was then allowed to cool to room temperature and concentrated in vacuo. The crude product was purified by reverse phase HPLC (Rainin $C_{18}$, 0% $CH_3CN$ to 30% $CH_3CN$ gradient, $CH_3CN/H_2O$, 0.1% TFA) and the bright yellow fractions containing the product were lyophilized after removal of $CH_3CN$ in vacuo to give 65 mg of yellow colored 3-Diethylaminomethyl-pyrimido[5,4-e][1,2,4]triazine-5,7-diamine 4 as the trifluoroacetate salt.

$^1$H NMR (DMSO-$d_6$, ppm): 9.10 (bs, 1H), 8.90 (bs, 1H), 8.15 (bs, 2H), 4.80 (s, 2H), 3.25 (q, 4H), 1.30 (t, 6H).

Example 6

3-Pyrrolidin-1-ylmethyl-pyrimido[5,4-e][1,2,4]triazine-5,7-diamine

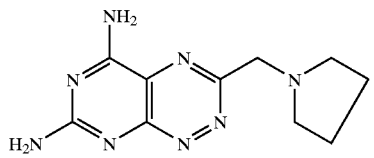

A mixture of 3-Chloromethyl-pyrimido[5,4-e][1,2,4]triazine-5,7-diamine 3 (70 mg; 0.33 mmol) and 1.0 mL of pyrrolidine were heated to 80° C. in a sealed tube for 7 h. The mixture was then allowed to cool to room temperature and concentrated in vacuo. The crude product was purified by reverse phase HPLC (Rainin $C_{18}$, 0% $CH_3CN$ to 30% $CH_3CN$ gradient, $CH_3CN/H_2O$, 0.1% TFA) and the bright yellow fractions containing the product were lyophilized after removal of $CH_3CN$ in vacuo to give 50 mg of yellow colored 3-Pyrrolidin-1-ylmethyl-pyrimido[5,4-e][1,2,4]triazine-5,7-diamine as the trifluoroacetate salt.

$^1$H NMR (DMSO-$d_6$, ppm): 9.15 (bs, 1H), 8.88 (bs, 1H), 8.20 (bs, 2H), 3.67 (s, 2H), 3.20 (bm, 2H), 1.85–2.10 (m, 4H).

Example 7

3-Piperidin-1-ylmethyl-pyrimido[5,4-e][1,2,4]triazine-5,7-diamine

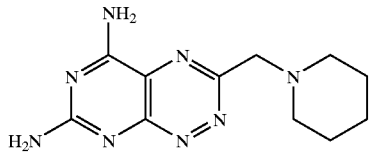

A mixture of 3-Chloromethyl-pyrimido[5,4-e][1,2,4]triazine-5,7-diamine 3 (70 mg; 0.33 mmol) and 1.0 mL of piperidine were heated to 80° C. in a sealed tube for 7 h. The mixture was then allowed to cool to room temperature and concentrated in vacuo. The crude product was purified by reverse phase HPLC (Rainin $C_{18}$, 0% $CH_3CN$ to 30% $CH_3CN$ gradient, $CH_3CN/H_2O$, 0.1% TFA) and the bright yellow fractions containing the product were lyophilized after removal of $CH_3CN$ in vacuo to give 111 mg of yellow colored 3-Piperidin-1-ylmethyl-pyrimido[5,4-e][1,2,4]triazine-5,7-diamine as the trifluoroacetate salt.

$^1$H NMR (DMSO-$d_6$, ppm): 9.18 (bs, 1H), 8.95 (bs, 1H), 8.30 (bs, 2H), 4.80 (s, 2H), 3.50 (bm, 2H), 3.10 (bm, 2H), 1.35–1.90 (m, 6H).

Example 8

3-Morpholin-4-ylmethyl-pyrimido[5,4-e][1,2,4]triazine-5,7-diamine

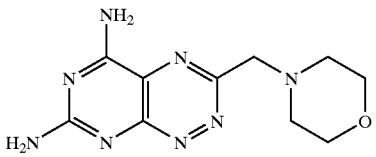

A mixture of 3-Chloromethyl-pyrimido[5,4-e][1,2,4]triazine-5,7-diamine 3 (200 mg; 0.95 mmol) and 2.0 mL of morpholine were heated to 80° C. in a sealed tube for 7 h. The mixture was then allowed to cool to room temperature and concentrated in vacuo. The crude product was purified by reverse phase HPLC (Rainin $C_{18}$, 0% $CH_3CN$ to 30% $CH_3CN$ gradient, $CH_3CN/H_2O$, 0.1% TFA) and the bright yellow fractions containing the product were lyophilized after removal of $CH_3CN$ in vacuo to give 261 mg of yellow colored 3-Morpholin-4-ylmethyl-pyrimido[5,4-e][1,2,4]triazine-5,7-diamine as the trifluoroacetate salt.

$^1$H NMR (DMSO-$d_6$, ppm): 9.25 (bs, 1H), 9.00 (bs, 1H), 8.30 (bs, 2H), 4.80 (s, 2H), 3.85 (m, 4H), 3.30 (m, 4H).

Example 9

3-(4-Methyl-piperazin-1-ylmethyl)-pyrimido[5,4-e][1,2,4]triazine-5,7-diamine

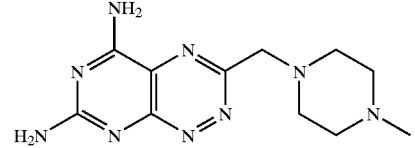

A mixture of 3-Chloromethyl-pyrimido[5,4-e][1,2,4]triazine-5,7-diamine 3 (200 mg; 0.95 mmol) and N-methylpiperazine (2.00 mL) were heated to 80° C. in a sealed tube for 7 h. The mixture was then allowed to cool to room temperature and concentrated in vacuo. The crude product was purified by reverse phase HPLC (Rainin $C_{18}$, 0% $CH_3CN$ to 30% $CH_3CN$ gradient, $CH_3CN/H_2O$, 0.1% TFA) and the bright yellow fractions containing the product were lyophilized after removal of $CH_3CN$ in vacuo to give 178 mg of yellow colored 3-(4-Methyl-piperazin-1-ylmethyl)-pyrimido[5,4-e][1,2,4]triazine-5,7-diamine as the trifluoroacetate salt.

$^1$H NMR ($D_2O$, ppm): 4.45 (s, 2H), 3.10–3.60 (m, 8H), 2.90 (s, 3H).

Example 10

3-(4-Benzyl-piperazin-1-ylmethyl)-pyrimido[5,4-e][1,2,4]triazine-5,7-diamine

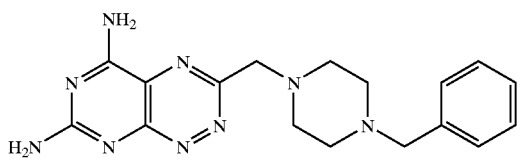

A mixture of 3-Chloromethyl-pyrimido[5,4-e][1,2,4]triazine-5,7-diamine 3 (48 mg; 0.23 mmol) and N-Benzylpiperazine (0.12 mL) in ethanol (0.1 mL) were heated to 90° C. in a sealed tube for 2 h. The mixture was then allowed to cool to room temperature and concentrated in vacuo. The crude product was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 26 mg of yellow colored 3-(4-Benzyl-piperazin-1-ylmethyl)-pyrimido[5,4-e][1,2,4]triazine-5,7-diamine as the trifluoroacetate salt.

$^1$H NMR (DMSO-$d_6$, ppm): 7.50 (m, 5H), 4.34 (s, 2H), 4.25 (s, 2H), 2.90–3.40 (m, 8H).

Example 11

3-(4-Naphthalen-2-ylmethyl-piperazin-1-ylmethyl)-pyrimido[5,4-e][1,2,4]triazine-5,7-diamine

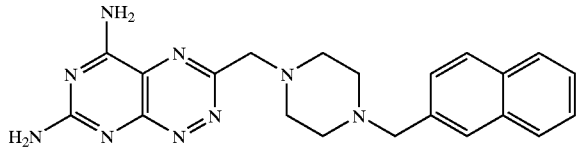

To a stirred solution of 3-Piperazin-1-ylmethyl-pyrimido[5,4-e][1,2,4]triazine-5,7-diamine TFA salt 5 (30 mg; 0.05 mmol; prepared in EXAMPLE 4) in dry DMF (1.0 mL) was added 2-bromomethylnaphthalene (17 mg; 0.075 mmol) followed by potassium carbonate (28 mg; 0.20 mmol). The mixture was allowed to stir for 24 h at room temperature then taken up into CH$_3$CN/H$_2$O/0.1% TFA. The mixture was purified by reverse phase HPLC (Rainin C$_{18}$, 0% CH$_3$CN to 30% CH$_3$CN gradient, CH$_3$CN/H$_2$O, 0.1% TFA) and the bright yellow fractions containing the product were lyophilized after removal of CH$_3$CN in vacuo to give 19 mg of yellow colored 3-(4-Naphthalen-2-ylmethyl-piperazin-1-ylmethyl)-pyrimido[5,4-e][1,2,4]triazine-5,7-diamine as the trifluoroacetate salt.

$^1$H NMR (DMSO-d$_6$, ppm): 9.37 (bs, 1H), 9.23 (bs, 1H), 8.20 (bs, 1H), 7.98 (m, 5H), 7.57 (m, 3H), 4.45 (bs, 2H), 4.15 (bs, 2H), 2.60–3.35 (m, 8H).

Example 12

3-(4-Naphthalen-1-ylmethyl-piperazin-1-ylmethyl)-pyrimido[5,4-e][1,2,4]triazine-5,7-diamine

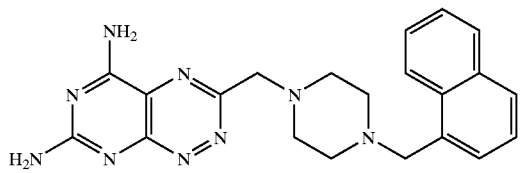

To a stirred solution of 3-Piperazin-1-ylmethyl-pyrimido[5,4-e][1,2,4]triazine-5,7-diamine TFA salt 5 (70 mg; 0.12 mmol; prepared in EXAMPLE 4) in dry DMF (1.0 mL) was added 1-chloromethylnaphthalene (0.023 mL; 0.18 mmol) followed by potassium carbonate (65 mg; 0.470 mmol). The mixture was allowed to stir for 24 h at room temperature then taken up into CH$_3$CN/H$_2$O/0.1% TFA. The mixture was purified by reverse phase HPLC (Rainin C$_{18}$, 0% CH$_3$CN to 30% CH$_3$CN gradient, CH$_3$CN/H$_2$O, 0.1% TFA) and the bright yellow fractions containing the product were lyophilized after removal of CH$_3$CN in vacuo to give 35 mg of yellow colored 3-(4-Naphthalen-1-ylmethyl-piperazin-1-ylmethyl)-pyrimido[5,4-e][1,2,4]triazine-5,7-diamine as the trifluoroacetate salt.

$^1$H NMR (DMSO-d$_6$, ppm): 9.36 (bs, 1H), 9.23 (bs, 1H), 8.53 (bs, 1H), 8.32 (m, 1H), 8.23 (bs, 1H), 8.00 (m, 2H), 7.60 (m, 4H), 4.68 (bs, 2H), 4.23 (bs, 2H), 2.80–3.40 (m, 8H).

Example 13

3-(4-Biphenyl-4-ylmethyl-piperazin-1-ylmethyl)-pyrimido[5,4-e][1,2,4]triazine-5,7-diamine

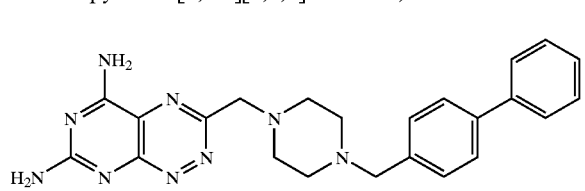

To a stirred solution of 3-Piperazin-1-ylmethyl-pyrimido[5,4-e][1,2,4]triazine-5,7-diamine TFA salt 5 (30 mg; 0.05 mmol; prepared in EXAMPLE 4) in dry DMF (1.0 mL) was added 4-chloromethylbiphenyl (15 mg; 0.08 mmol) followed by potassium carbonate (28 mg; 0.20 mmol). The mixture was allowed to stir for 24 h at room temperature then taken up into CH$_3$CN/H$_2$O/0.1% TFA. The mixture was purified by reverse phase HPLC (Rainin C$_{18}$, 0% CH$_3$CN to 30% CH$_3$CN gradient, CH$_3$CN/H$_2$O, 0.1% TFA) and the bright yellow fractions containing the product were lyophilized after removal of CH$_3$CN in vacuo to give 20 mg of yellow colored 3-(4-Biphenyl4-ylmethyl-piperazin-1-ylmethyl)-pyrimido[5,4-e][1,2,4]triazine-5,7-diamine as the trifluoroacetate salt.

$^1$H NMR (DMSO-d$_6$, ppm): 9.60 (s, 1H), 9.43 (s, 1H), 8.83 (bs, 1H), 8.53 (bs, 1H), 7.35–7.82 (m, 9H), 4.33 (s, 2H), 4.15 (s, 2H), 2.70–3.40 (m, 8H).

Example 14

3-[4-(2-Chloro-benzyl)-piperazin-1-ylmethyl]-pyrimido[5,4-e][1,2,4]triazine-5,7-diamine

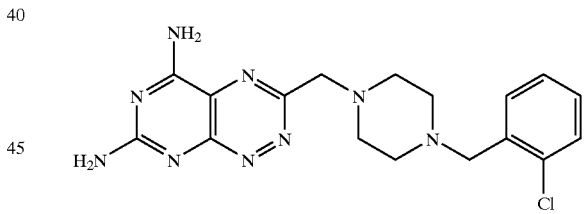

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added o-chlorobenzyl chloride (0.015 mL; 0.12 mmol) followed by potassium carbonate (55 mg; 0.40 mmol). The mixture was allowed to stir for 24 h at room temperature then taken up into CH$_3$CN/H$_2$O/0.1% TFA. The mixture was purified by reverse phase HPLC (Rainin C18, 0% CH$_3$CN to 50% CH$_3$CN gradient, CH$_3$CN/H$_2$O, 0.1% TFA). and the bright yellow fractions containing the product were lyophilized after removal of CH$_3$CN in vacuo to give 17 mg of yellow colored 3-[4-(2-Chloro-benzyl)-piperazin-1-ylmethyl]-pyrimido[5,4-e][1,2,4]triazine-5,7-diamine as the trifluoroacetate salt.

$^1$H NMR (MeOH-d$_4$, ppm): 7.40–7.70 (m, 4H), 4.44 (s, 2H), 4.36 (s, 2H), 2.80–3.40 (m, 8H).

Example 15

3-[4-(3-Chloro-benzyl)-piperazin-1-ylmethyl]-pyrimido[5,4-e][1,2,4]triazine-5,7-diamine

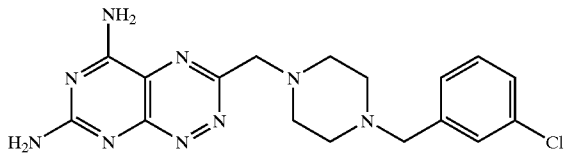

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added m-chlorobenzyl chloride (0.015 mL; 0.12 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 9 mg of yellow colored 3-[4-(3-Chloro-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.40–7.58 (m, 4H), 4.32 (s, 4H), 2.80–3.40 (m, 8H).

Example 16

3-[4-(4-Chloro-benzyl)-piperazin-1-ylmethyl]-pyrimido[5,4-e][1,2,4]triazine-5,7-diamine

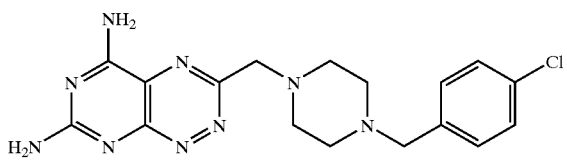

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added p-chlorobenzyl chloride (29 mg; 0.18 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 21 mg of yellow colored 3-[4-(4-Chloro-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 8.20 (m, 4H), 4.30 (s, 4H), 2.88–3.40 (m, 8H).

Example 17

3-[4-(3-Methoxy-benzyl)-piperazin-1-ylmethyl]-pyrimido[5,4-e][1,2,4]triazine-5,7-diamine

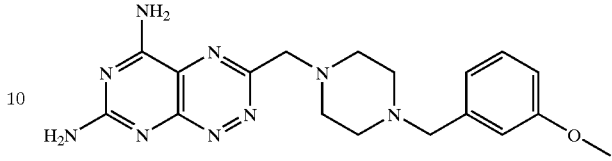

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added m-methoxybenzyl chloride (19 mg; 0.12 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H20$, 0.1% TFA) and the bright yellow fractions containing the product were lyophilized after removal of $CH_3CN$ in vacuo to give 30 mg of yellow colored 3-[4-(3-Methoxy-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.40 (m, 1H), 7.06 (m, 3H), 4.30 (s, 2H), 4.23 (s, 2H), 3.81 (s, 3H), 2.80–3.40 (m, 8H).

Example 18

3-[4-(3-Fluoro-benzyl)-piperazin-1-ylmethyl]-pyrimido[5,4-e][1,2,4]triazine-5,7-diamine

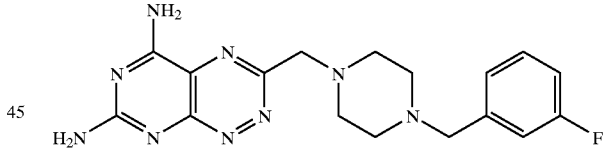

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added m-fluorobenzyl chloride (0.0143 mL; 0.12 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 11 mg of yellow colored 3-[4-(3-Fluoro-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.18–7.60 (m, 4H), 4.33 (s, 2H), 4.27 (s, 2H), 2.83–3.38 (m, 8H).

Example 19

3-[4-(3-Trifluoromethyl-benzyl)-piperazin-1-ylmethyl]-pyrimido[5,4-e][1,2,4]triazine-5,7-diamine

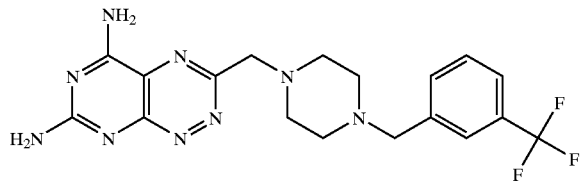

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added m-trifluoromethylbenzyl bromide (0.021 mL; 0.14 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 13 mg of yellow colored 3-[4-(3-Trifluoromethyl-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.63–7.92 (m, 4H), 4.38 (s, 2H), 4.32 (s, 2H), 2.85–3.38 (m, 8H).

Example 20

3-[4-(4-Trifluoromethyl-benzyl)-piperazin-1-ylmethyl]-pyrimido[5,4-e][1,2,4]triazine-5,7-diamine

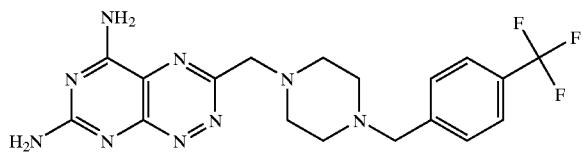

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added p-trifluoromethylbenzyl bromide (0.021 mL; 0.14 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 22 mg of yellow colored 3-[4-(4-Trifluoromethyl-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.77 (m, 4H), 4.37 (s, 2H), 4.33 (s, 2H), 2.90–3.38 (m, 8H).

Example 21

3-[4-(3-Bromo-benzyl)-piperazin-1-ylmethyl]-pyrimido[5,4-e][1,2,4]triazine-5,7-diamine

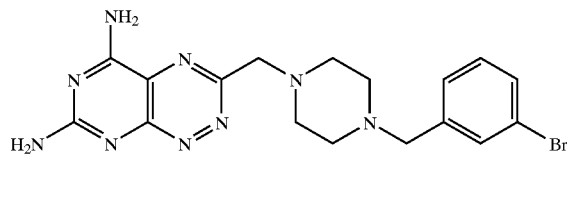

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added m-bromobenzyl bromide (34 mg; 0.14 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 15 mg of yellow colored 3-[4-(3-Bromo-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.38–7.80 (m, 4H), 4.30 (s, 4H), 2.85–3.38 (m, 8H).

Example 22

3-[4-(3-Cyano-benzyl)-piperazin-1-ylmethyl]-pyrimido[5,4-e][1,2,4]triazine-5,7-diamine

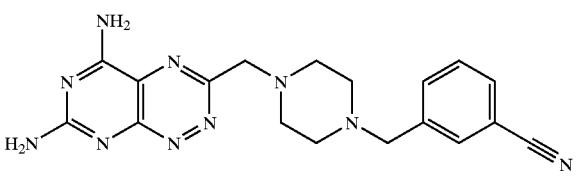

To a stirred solution of 3-Piperazin-1-ylmethyl-pyrimido[5,4-e][1,2,4]triazine-5,7-diamine TFA salt 5 (50 mg; 0.08 mmol; prepared in EXAMPLE 4) in dry DMF (1.0 mL) was added m-cyanobenzyl bromide (23 mg; 0.18 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 12 mg of yellow colored 3-[4-(3-Cyano-benzyl)-piperazin-1-ylmethyl]-pyrimido[5,4-e][1,2,4]triazine-5,7-diamine as the trifluoroacetate salt.

$^1$H NMR (MeOH-$d_4$, ppm): 7.60–7.92 (m, 4H), 4.37 (s, 2H), 4.27 (s, 2H), 2.95–3.35 (m, 8H).

Example 23

3-[4-(2,4-Dimethyl-benzyl)-piperazin-1-ylmethyl]-pyrimido[5,4-e][1,2,4]triazine-5,7-diamine

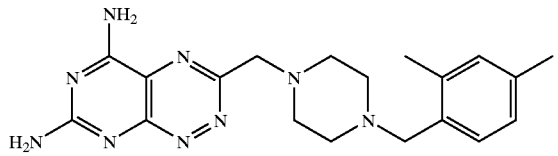

To a stirred solution of 3-Piperazin-1-ylmethyl-pyrimido [5,4-e][1,2,4]triazine-5,7-diamine TFA salt 5 (50 mg; 0.08 mmol; prepared in EXAMPLE 4) in dry DMF (1.0 mL) was added 2,4-dimethylbenzyl chloride (0.020 mL; 0.13 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 10 mg of yellow colored 3-[4-(2,4-Dimethyl-benzyl)-piperazin-1-ylmethyl]-pyrimido[5,4-e][1,2,4]triazine-5,7-diamine as the trifluoroacetate salt. $^1H$ NMR (dmso-$d_6$, ppm): 9.40 (bs, 1H), 8.17 (bs, 2H), 7.00–7.40 (m, 3H), 4.28 (bs, 2H), 4.10 (bs, 2H), 2.95–3.35 (m, 8H), 2.34 (s, 3H), 2.28 (s, 3H).

Example 24

3-[4-(4-Ethyl-2-methyl-naphthalen-1-ylmethyl)-piperazin-1-ylmethyl]-pyrimido[5,4-e][1,2,4]triazine-5,7-diamine

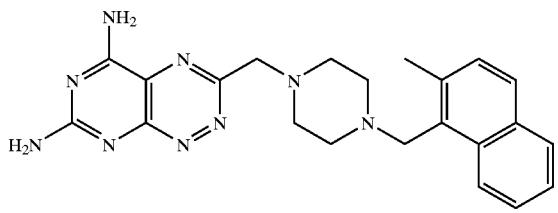

To a stirred solution of 3-Piperazin-1-ylmethyl-pyrimido [5,4-e][1,2,4]triazine-5,7-diamine TFA salt 5 (50 mg; 0.08 mmol; prepared in EXAMPLE 4) in dry DMF (1.0 mL) was added 1-Chloromethyl-2-methyl-Naphthalene (34 mg; 0.18 mmol) followed by potassium carbonate (55 mg; 0.40 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 23 mg of yellow colored 3-[4-(4-Ethyl-2-methyl-naphthalen-1-ylmethyl)-piperazin-1-ylmethyl]-pyrimido[5,4-e][1,2,4]triazine-5,7-diamine as the trifluoroacetate salt.

$^1H$ NMR (MeOH-$d_4$, ppm): 8.07 (m, 1H), 7.92 (m, 2H), 7.40–7.50 (m, 3H), 4.90 (s, 2H), 4.37 (s, 2H), 2.70 (s, 3H), 2.80–3.45 (m, 8H).

Example 25

3-[4-(4-Benzyloxy-benzyl)-piperazin-1-ylmethyl]-pyrimido[5,4-e][1,2,4]triazine-5,7-diamine

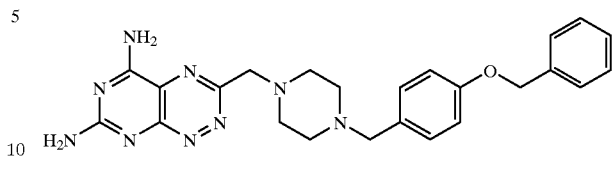

To a stirred solution of 3-Piperazin-1-ylmethyl-pyrimido [5,4-e][1,2,4]triazine-5,7-diamine TFA salt 5 (50 mg; 0.08 mmol; prepared in EXAMPLE 4) in dry DMF (1.0 mL) was added 1-Chloromethyl-2-methyl-Naphthalene (27 mg; 0.12 mmol) followed by potassium carbonate (58 mg; 0.42 mmol). The mixture was allowed to stir for 24 h at room temperature then taken up into $CH_3CN/H_2O/0.1\%$ TFA. The mixture was purified by reverse phase HPLC (Rainin $C_{18}$, 0% $CH_3CN$ to 50% $CH_3CN$ gradient, $CH_3CN/H_2O$, 0.1% TFA) and the bright yellow fractions containing the product were lyophilized after removal of $CH_3CN$ in vacuo to give 23 mg of yellow colored 3-[4-(4-Benzyloxy-benzyl)-piperazin-1-ylmethyl]-pyrimido[5,4-e][1,2,4]triazine-5,7-diamine as the trifluoroacetate salt.

$^1H$ NMR (dmso-$d_6$, ppm): 9.63 (s, 1H), 9.50 (s, 1H), 8.91 (bs, 1H), 8.77 (bs, 1H), 7.40 (m, 7H), 7.05 (m, 2H), 5.12 (s, 2H), 4.25 (s, 2H), 4.17 (s, 2H), 2.60–3.40 (m, 8H).

Example 26

In Vitro Inhibition of PTP1B

Human PTP1B (1–321) was cloned from a human cDNA library using conventional molecular biology techniques. The cDNA sequence was identical to the published human PTP1B sequence (Accession number M33689). The protein was expressed and purified from *E. coli* as described by Barford D. et.al J. Mol Biol (1994) 239, 726–730.

PTPase Assays

The measurement of PTPase activity was carried out using one of two methods:

The first method for the measurement of PTP1B inhibitory activity a tyrosine phosphorylated peptide based on the amino acid sequence of insulin receptor tyrosine autophosphorylation site 1146 (TRDI(pY)E) was used as substrate. The reaction conditions were as follows:

PTP1B (0.5–2 nM) was incubated with compound for 15 min in buffer containing 37.5 mM Mes buffer pH 6.2, 140 mM NaCl, 0.05% BSA and 300 nM DTT. The reaction was started by the addition of 50 μM substrate. After 20 min at room temperature (22–25° C.) the reaction was stopped with KOH and the amount of free phosphate measured using Malachite Green as previously described. (Harder et al. 1994 Biochem J. 298; 395).

The second method was used for the measurement of general PTPase inhibitory activity across a panel of PTPases. The substrate (6,8-difluoro4-methylumbelliferyl phosphate (DiFMUP; from Molecular Probes) was used at the Km for each enzyme. The buffer conditions were identical to those of the above Malachite Green assay except that 37.5 mM diethylglutarate pH 6.2 was used instead of MES. The reaction was stopped with KOH. In this case the dephosphoryated product becomes fluorescent and the fluorescense is read. (Excitiation: 360 mM/Emmission: 460 nM).

For kinetic experiments the same buffer conditions were used except that the reaction was started using enzyme and the reaction stopped after 10 minutes.

As measured in the above in vitro assays, all of the compounds of Examples 4–25 had a PTP1B IC$_{50}$ of less than 30 µM.

Example 27

Effects of Compounds on Blood Glucose Levels in Mouse Model

To measure the antidiabetic effect compounds were tested in well established rodent in vivo models of type 2 diabetes and obesity.

Obese ob/ob Mice

Male or female ob/ob (C57BL6/J) mice (Diabetologia 14, 141–148 (1978)) (Jackson Labs) 40–50 g were used to assess the effects of compounds on glucose lowering in addition to triglyceride lowering. Mice were presorted into groups of 10–12 based on their glucose levels as well as their body weight. The mice were maintained on a normal rodent chow diet with water ad libitum. Mice received compound daily by gavage (suspended in 1% Na-CMC) for five days. Immediately prior to dosing, a predose blood glucose reading was taken on day one by snipping off a portion of the tail and collecting blood from the tail vein. Two hours post treatment on day five another measurement for glucose was made by the same method. The animals were then anesthetized and sacrificed by exsanguination. Blood and tissues were collected for analysis. Compounds are considered active when they exhibit a statistically significant (p≦0.05) decrease in blood glucose compared to vehicle treated mice.

Diet Induced Obese C57BL6/J Mice (DIO Mice)

Mice that have type 2 diabetes can be generated by maintaining them on a high fat diet for a 4–6 months (Diabetes 37:1163–67 September 1988). Male C57BI6/J mice (age 3–4 weeks ) were placed on high fat diet for 4–6 weeks. At this time they were hyperglycemic and hyperinsulinemic and weighed 40–50 g. DIO mice (n=6) were weighed and fasted for a two hour period prior to oral treatment. Immediately prior to dosing by gavage, a pre dose (time zero) glucose reading was obtained from the tail vein as described above. Mice were treated with compound once a day for 5 days. Vehicle mice were not given the compound. On day five glucose was measured prior to dosing (0 time) and 2 hours and 4 hours after dosing. Insulin and triglycerides were measured at 4 hour post dose. Compounds were considered active if the effect of the compounds in the animals showed a statistically significant (p≦0,05) glucose, insulin and triglyceride lowering compared to the vehicle treated animals.

Compounds of examples 5, 10 and 13 have been tested in vivo in mice in accordance with the procedure of Example 27 and have shown blood glucose reductions of at least 15%.

We claim:

1. A compound of the formula:

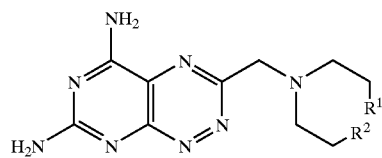

I wherein
R$^1$ and R$^2$ are individually selected from the group consisting of hydrogen, or
R$^1$ and R$^2$ together form a bond, —CH$_2$—, —O—, —NH— or —N—R$^3$, R$^3$ is lower alkyl or —CH$_2$—Ar, and
Ar is selected from the group consisting of unsubstituted phenyl; unsubstituted naphthyl; phenyl mono- or bi-substituted with lower alkyl, lower alkoxy, aryl, cycloalkyl, lower alkyl-aryl, lower alkoxy-aryl, lower alkyl-cycloalkyl, lower alkoxy-cycloalkyl, halo, cyano or trifluoromethyl; and naphthyl mono- or bi-substituted with lower alkyl, lower alkoxy, aryl, cycloalkyl, lower alkyl-aryl, lower alkoxy-aryl, lower alkyl-cycloalkyl, lower alkoxy-cylcoalkyl or halo;

or pharmaceutically acceptable salts thereof.

2. The compound of claim 1, having the formula:

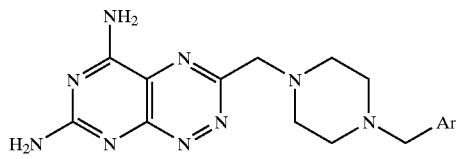

II wherein Ar is selected from the group consisting of unsubstituted phenyl;

unsubstituted naphthyl; phenyl mono- or bi-substituted with lower alkyl, lower alkoxy, aryl, cycloalkyl, lower alkyl-aryl, lower alkoxy-aryl, lower alkyl-cycloalkyl, lower alkoxy-cycloalkyl, halo, cyano or trifluoromethyl; and naphthyl mono- or bi-substituted with lower alkyl, lower alkoxy, aryl, cycloalkyl, lower alkyl-aryl, lower alkoxy-aryl, lower alkyl-cycloalkyl, lower alkoxy-cylcoalkyl or halo;

or pharmaceutically acceptable salts of compounds of formula II.

3. The compound of claim 2, wherein Ar is unsubstituted phenyl or unsubstituted naphthyl.

4. The compound of claim 2, wherein Ar is phenyl mono-substituted with lower alkyl, lower alkoxy, aryl, cycloalkyl, lower alkyl-aryl, lower alkoxy-aryl, halo, cyano or trifluoromethyl.

5. The compound of claim 4, wherein Ar is phenyl mono-substituted with lower alkyl, lower alkoxy, halo, cyano or trifluoromethyl.

6. The compound of claim 2, wherein Ar is phenyl bi-substituted with lower alkyl, lower alkoxy, halo or cyano.

7. The compound of claim 2, wherein Ar is naphthyl mono-substituted with lower alkyl, lower alkoxy, lower alkyl-aryl, lower alkoxy-aryl or halo.

8. The compound of claim 7, wherein Ar is naphthyl mono-substituted with lower alkyl, lower alkoxy or halo.

9. The compound of claim 2, wherein Ar is naphthyl bi-substituted with lower alkyl, lower alkoxy or halo.

10. The compound of claim 1, having the formula: 3-diethylaminomethyl-pyrimido[5,4-e][1 ,2,4]triazine-5,7-diamine.

11. The compound of claim 1, having the formula: 3-(4-benzyl-piperazin-1-ylmethyl)-pyrimido[5,4-e][1 ,2,4]triazine-5,7-diamine.

12. The compound of claim 1, having the formula: 3-(4-naphthalen-2-ylmethyl-piperazin-1-ylmethyl)-pyrimido[5,4-e][1 ,2,4]triazine-5,7-diamine.

13. The compound of claim 1, having the formula: 3-(4-naphthalen-1-ylmethyl-piperazin-1-ylmethyl)-pyrimido[5,4-e][1 ,2,4]triazine-5,7-diamine.

14. The compound of claim 1, having the formula: 3-(4-biphenyl4-ylmethyl-piperazin-1-ylmethyl)-pyrimido[5,4-e][1 ,2,4]triazine-5 ,7-diamine.

15. The compound of claim 1, having the formula: 3-[4-(2,4-dimethyl-benzyl)-piperazin-1-ylmethyl]-pyrimido[5,4-e][1,2,4]triazine-5,7-diamine.

16. The compound of claim 1, having the formula: 3-[4-(4-ethyl-2-methyl-naphthalen-1-ylmethyl)-piperazin-1-ylmethyl]-pyrimido[5,4-e][1,2,4]triazine-5,7-diamine.

17. The compound of claim 1, having the formula: 3-[4-(4-benzyloxy-benzyl)-piperazin-1-ylmethyl]-pyrimido[5,4-e][1,2,4]triazine-5,7-diamine.

* * * * *

UNITED STATES PATENT AND TRADEMARK OFFICE
CERTIFICATE OF CORRECTION

PATENT NO. : 6,642,381 B2
DATED : November 4, 2003
INVENTOR(S) : Kevin Richard Guertin and Lina Quattrocchio Setti It is certified that error appears in the above-identified patent and that said Letters Patent is hereby corrected as shown below:

<u>Title page,</u>
Item [73], "Assignee: Hoffman-La Roche Inc., Nutley, NJ (US)" should be
-- Assignee: Hoffmann-La Roche Inc., Nutley, NJ (US) --

Signed and Sealed this

Thirtieth Day of March, 2004

JON W. DUDAS
*Acting Director of the United States Patent and Trademark Office*